United States Patent [19]

Milligan et al.

[11] Patent Number: 5,275,156

[45] Date of Patent: Jan. 4, 1994

[54] REUSABLE HEAT RELEASING PACK

[75] Inventors: Andrew J. Milligan, Berwyn; Robert A. Lewis, King of Prussia, both of Pa.

[73] Assignee: Nova Design Partners, L.P., Malvern, Pa.

[21] Appl. No.: 912,449

[22] Filed: Jul. 13, 1992

[51] Int. Cl.⁵ .......................... F24J 1/00; A61F 7/00
[52] U.S. Cl. .................... 607/114; 126/204; 126/263 C
[58] Field of Search ................... 128/399–; 126/263, 204, 206; 422/245; 62/3, 530

[56] References Cited

U.S. PATENT DOCUMENTS

| | | |
|---|---|---|
| 708,549 | 9/1902 | Heiliger . |
| 3,643,665 | 2/1972 | Caillouette . |
| 3,951,127 | 4/1976 | Watson . |
| 4,077,390 | 3/1978 | Stanley . |
| 4,451,383 | 5/1984 | Arrhenius . |
| 4,580,547 | 4/1986 | Kapralis . |
| 4,780,117 | 10/1988 | Lahey ............................ 126/263 |
| 4,829,980 | 5/1989 | Smith ............................ 126/263 |
| 4,860,729 | 8/1989 | Benson et al. . |
| 4,872,442 | 10/1989 | Manker ........................... 126/263 |
| 4,953,628 | 9/1990 | Yamashita ...................... 126/263 |
| 5,056,589 | 10/1991 | Hettel et al. ................... 126/263 |
| 5,058,563 | 10/1991 | Manker ........................... 126/263 |

*Primary Examiner*—Mark S. Graham
*Attorney, Agent, or Firm*—Caesar, Rivise, Bernstein, Cohen & Pokotilow, Ltd.

[57] ABSTRACT

A reusable device for delivering a release of heat to an area such as a body portion. The device comprises a flexible, fluid-tight container holding a liquid which releases heat upon crystallization such as sodium acetate tetrahydrate. A trigger located within the container initiates the crystallization of the liquid to release the latent heat. The trigger comprises a plurality of rigid objects held within a receptacle located within the container. The receptacle is in fluid communication with the container so that the plurality of rigid objects are in contact with the liquid. The trigger initiates the crystallization of the liquid when pressure is applied to the plurality of rigid objects such as by squeezing the trigger between one's fingers.

9 Claims, 2 Drawing Sheets

REUSABLE HEAT RELEASING PACK

BACKGROUND OF THE INVENTION

The present invention relates generally to an apparatus for initiating the crystallization of a supercooled material such as those used for phase-change thermal energy storage. Such crystallization causes the supercooled material to change from its high-temperature phase to its low-temperature phase very rapidly, and in doing so, surrender its latent heat of transition.

The principles of thermal energy storage in phase-changer materials is well known. As the materials are heated from an initial phase, such as the solid phase, to a stage, such as the liquid phase, energy is absorbed. In the temperature range at which the material changes from one phase to another, more energy is required to raise the temperature an additional increment than to raise the temperature by the same increment when the material is not changing phase. This additional energy required at the phase change of the material is called the latent heat of transition.

The heat required for the phase change from liquid to gas is called the latent heat of vaporization. The heat required for the phase change from solid to liquid and given up in the reverse phase change from liquid to solid is known as the latent heat of fusion. When a material cools, the energy absorbed at the phase-change point is normally given up. Some materials will cool well below the normal phase change temperature, but still retain the latent heat of transition and remain in the higher temperature phase or state. For example, some materials under some circumstances may be cooled below the temperatures at which they normally change from liquid to solid, yet remain in the liquid state, thus still retain the latent heat of fusion. A material in this condition is said to be undercooled or supercooled. It is possible to create conditions in an undercooled material that will cause it to change very rapidly from the high-temperature phase to the low-temperature phase, thus giving up the energy stored as the latent heat of transition or fusion rapidly. The energy so release may be put to practical use in many ways.

Various types of trigger devices have been utilized in the past to initiate the reaction process necessary to obtain the stored heat when desired. For example, in U.S. Pat. No. 708,549 (Heiliger) is disclosed a trigger device which utilizes the frictional rubbing together of two opposed surfaces to initiate a crystallization reaction which releases heat.

In U.S. Pat. No. 4,860,729 is disclosed an apparatus to nucleate the crystallization of undercooled materials. That patent discloses a trigger device which traps a crystallite of the material between two solid objects and retains it there by pressing the objects together with enough force to create sufficient pressure to keep the crystallite isolated between the two solid objects when it is immersed in the phase-change material and to keep it from melting. Thereafter the crystallite is exposed to the supercooled, phase-change material by releasing the pressure and allowing the supercooled, phase-change material to contact the crystallite. It appears that this device may be lacking in flexibility to various types of applications because it requires the constant isolation of the crystallite from the surrounding solution in order to maintain the integrity of the trigger mechanism.

U.S. Pat. No. 4,077,390 (Stanley) discloses a heat pack enclosing supercoolable aqueous sodium acetate solution together with a metallic activator strip which initiates crystallization by the bending of the activator strip.

Other types of therapeutic heating devices which utilize heat generated from a chemical reaction or change are also disclosed in the following U.S. Patents: U.S. Pat. No. 3,643,665 (Caillouette) ; U.S. Pat. No. 3,951,127 (Watson et al.); U.S. Pat. No. 4,451,383 (Arrhenius); U.S. Pat. No. 4,580,547 (Kapralis)

Accordingly, a need exists for a reusable heat pack device to be used in variety of applications.

OBJECTS OF THE INVENTION

Accordingly, it is a general object of this invention to provide a reusable heat pack which overcomes the disadvantages of the prior art.

It is a further object of this invention to provide a heat pack which has a reliable trigger mechanism.

It is another object of this invention to provide a heat pack having a trigger mechanism which is easy and inexpensive to manufacture and assemble.

SUMMARY OF THE INVENTION

These and other objects of this invention are achieved by providing a reusable device for delivering a release of heat to an area such as a body portion. The device comprises a flexible, fluid-tight container holding a liquid which releases heat upon crystallization such as sodium acetate tetrahydrate. A trigger located within the container initiates the crystallization of the liquid to release the latent heat. The trigger comprises a plurality of rigid objects held within a receptacle located within the container. The receptacle is in fluid communication with the container so that the plurality of rigid objects are in contact with the liquid. The trigger initiates the crystallization of the liquid when pressure is applied to the plurality of rigid objects such as by squeezing the trigger between one's fingers.

DESCRIPTION OF THE DRAWINGS

Other objects and many attendant features of this invention will become readily appreciated as the same becomes better understood by reference to the following detailed description when considered in connection with the accompanying drawings wherein.

DETAILED DESCRIPTION OF THE PREFERRED EMBODIMENT

Figure 1:
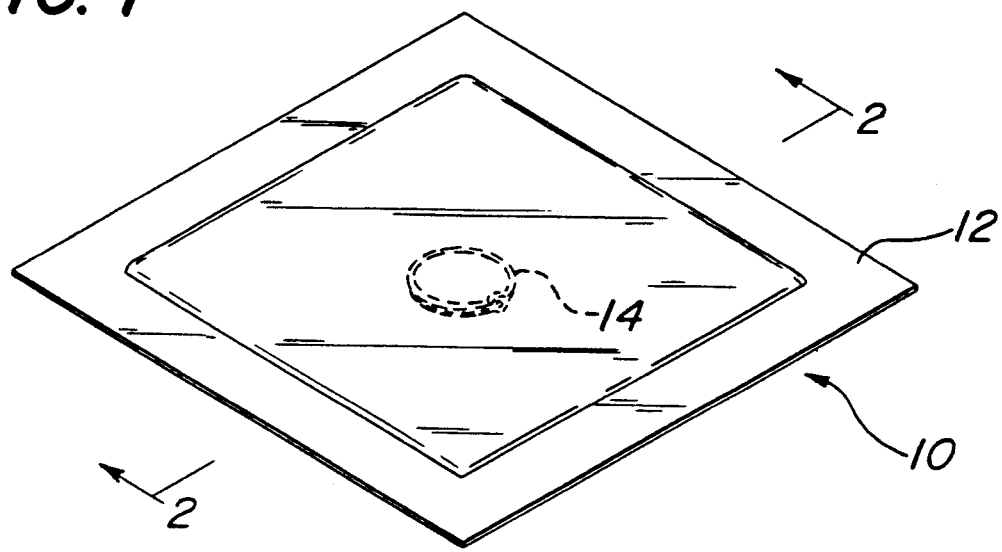
FIG. 1 is an isometric view of a device constructed in accordance with the present invention.
Figure 2:
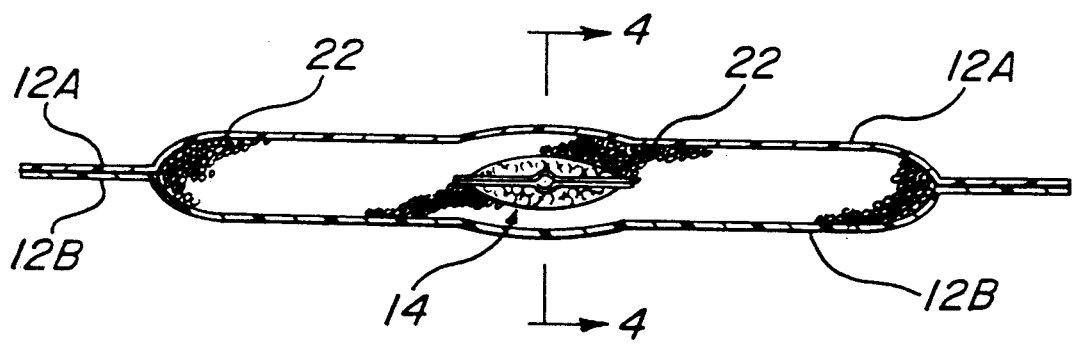
FIG. 2 is an enlarged cross sectional view of a device constructed in accordance with the present invention, taken along line 2—2 of FIG. 1, with the phase change material in a crystalline form.
Figure 3:
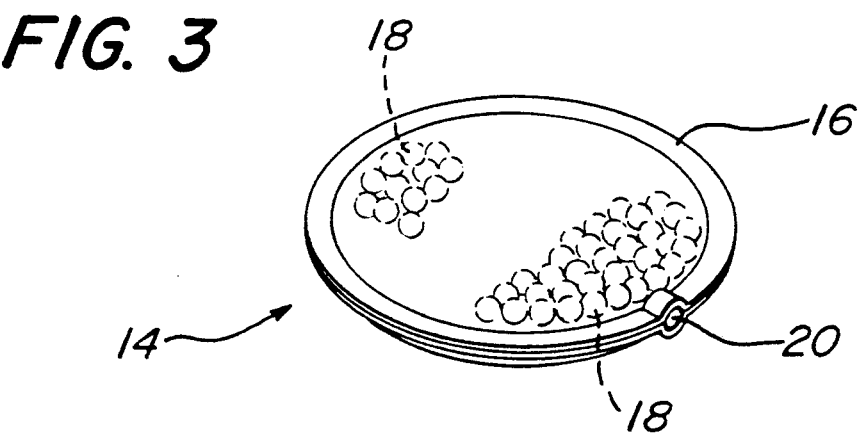
FIG. 3 is a side view of one embodiment of the trigger of the present invention.

Referring now to various figures of the drawings where like reference numerals refer to like parts, there is shown at 10 in FIG. 1, a device constructed in accordance with this invention. The device 10, includes a sealed container 12 preferably comprised of a flexible material such as plastic. The embodiment of the device 10 shown in FIGS. 1 and 2, has an upper and lower surface 12A and 12B, respectively comprised of a flexible material which is sealed about the periphery.

Within the sealed container 12 is a phase change material 22, such as sodium acetate tetrahydrate. In its supercooled state, the material is a liquid storing the latent heat of fusion. When triggered, the material will solidfy and, release heat to the desired area.

In order to initiate the crystallization process, a trigger mechanism 14 is provided as shown in FIGS. 2-5. The trigger 14, basically comprises a receptacle 16 containing a plurality of generally spherical objects 18 therein. The receptacle 16 is in fluid communication with the sealed container 12 via opening 20, so that the phase change material is in contact with the spherical objects which initiate the desired crystallization process. Although the receptacle is shown as being only partially filled with spherical objects, it is desirable to have the receptacle generally be filled with spherical objects to permit them to be in close proximity with one another.

Figure 5:
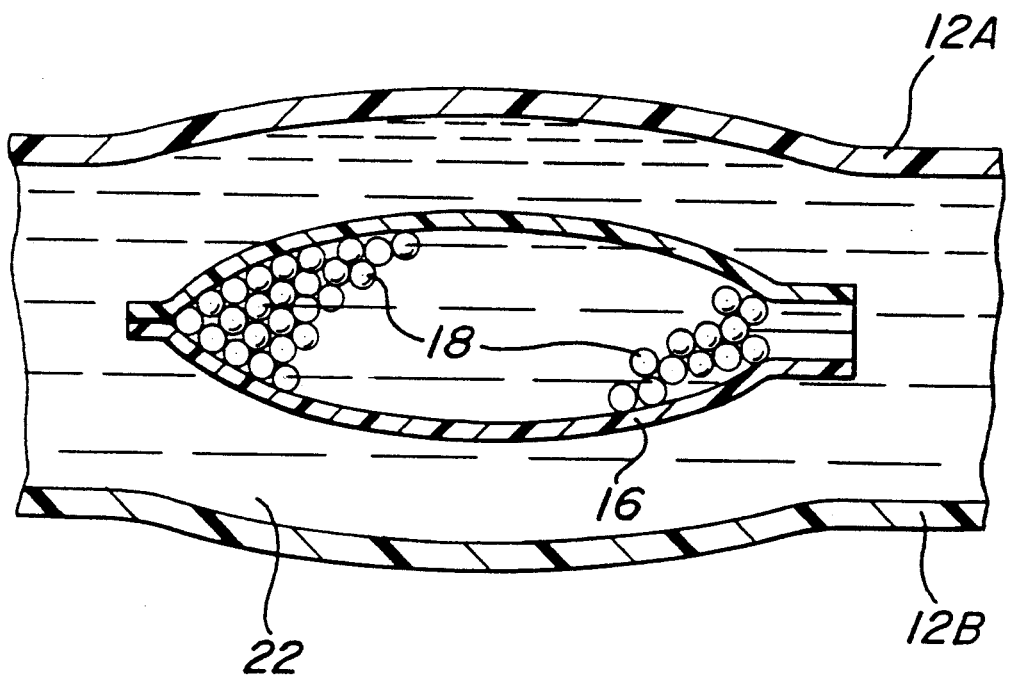
FIG. 5 is an enlarged cross-sectional view of a device constructed in accordance with the present invention, with the phase change material in a liquid form.

In order to activate the device, the phase change material 22, in this case, sodium acetate tetrahydrate, should be in its liquid state so that it is in contact with the spherical objects 18 as shown in FIG. 5. To initiate the crystallization process, the spherical objects 18 may be compressed or squeezed between one's fingers or some other object to permit them to rub together and initiate the crystallization. As the material solidifies, heat is given off and may be utilized accordingly. For example, the heat may be used in a therapeutic fashion and applied as desired to the various body parts.

Figure 4:
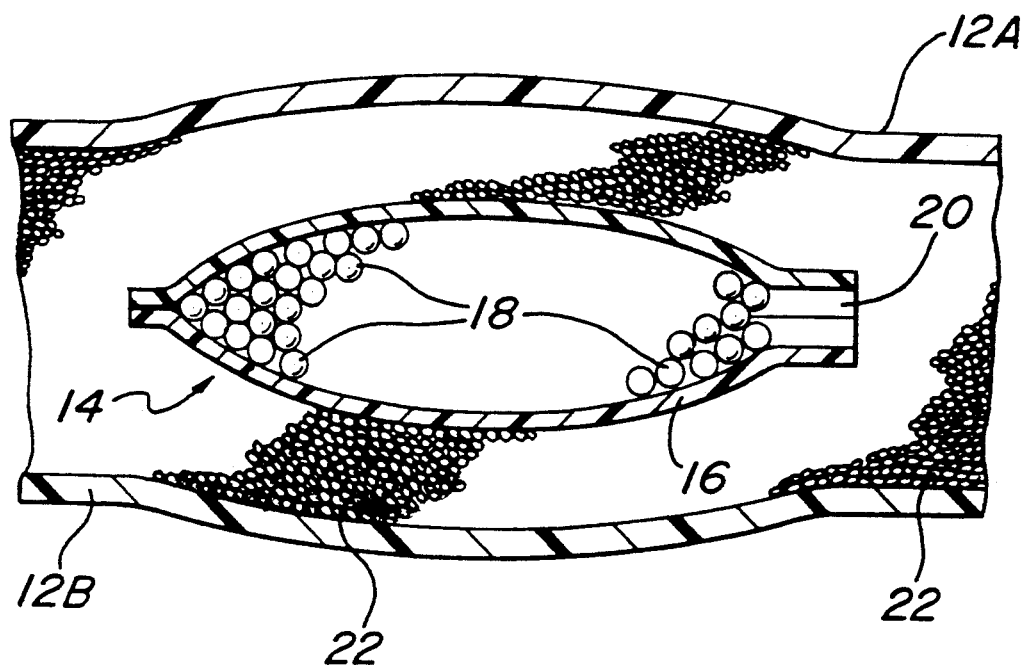
FIG. 4 is an enlarged cross-sectional view of a device constructed in accordance with the present invention, taken along line 4—4 of FIG. 2, with the phase change material in a crystalline form.

After the crystallization is completed as shown in FIG. 4, the crystallization process may be reversed by heating the device 10 in any suitable fashion, such as in water, etc. The device may thereafter be stored until needed as shown in FIG. 5.

It should be readily apparent to those skilled in the art that almost any suitable phase change material and amount thereof, may be utilized and that therefore the present invention is not limited to only sodium acetate tetrahydrate, but may include sodium acetate, sodium thiosulfate, trimethylol ethane hydrate and other materials known in the art.

In addition, the size of the container 12 is merely exemplary, and it should be readily apparent that almost any shaped container may be used and that the container may be shaped to conform to a body part for ease of application thereto. Typically the container is formed of a resilient material such as plastic which may be bound or sealed at its periphery in accordance with conventional methods, e.g., heat sealing.

The trigger 14 utilizable in the present invention can also be of almost any shape to contain the plurality of spherical objects 18 therein in relatively close proximity to one another, so that they will contact one another when pressure is applied, e.g., by squeezing with one's fingers. In one embodiment, the trigger may contain between 25 to 50 of such spherical objects, although this number is merely exemplary. The trigger may also be comprised of any type of resilient material such as plastic, which may be sealed about its periphery, except for opening 20, by conventional methods such as by heat sealing, etc.

In a preferred embodiment, the spherical objects are of an approximate diameter of 1.5 mm and may be comprised of a ceramic, glass or other suitable material depending upon the circumstances of use. Other types and sizes of materials may also be utilized depending upon availability and cost.

The receptacle for the trigger may also be comprised of any suitable generally flexible material and may be of various shapes and dimensions. The receptacle is preferably circular or cylindrical with a plug at each end thereof with one of the plugs in fluid communication with the container. One type of suitable material is a plastic such as polyethylene which is sufficiently flexible enough to be slightly bent by one's fingers as the spherical objects are compressed, squeezed, etc. The receptacle should be in fluid communication with the container to permit the crystallization process to proceed into the container contents. The opening in receptacle can be of any suitable dimension as long as the spherical objects contained therein are retained by the receptacle. In addition, it is desirable to dimension the receptacle so that the spherical objects may be retained in relatively close proximity to one another, so that they will contact one another when rubbed or squeezed together.

Without further elaboration the foregoing will so fully illustrate our invention that others may, by applying current or future knowledge, adapt the same for use under various conditions of service.

We claim:

1. A reusable device for delivering a release of heat to an area, the device comprising:
   (a) a liquid which releases heat upon crystallization;
   (b) a flexible, fluid-tight container to hold the liquid therein;
   (c) a trigger to initiate the crystallization of the liquid, the trigger comprising a plurality of rigid objects held in generally close proximity to one another within a receptacle located within the container, the rigid objects being comprised of a material selected from the group consisting of ceramic and glass, and wherein the receptacle is in fluid communication with the container so that the plurality of rigid objects are in contact with the liquid, the trigger initiating the crystallization of the liquid when pressure is applied to the plurality of rigid objects.

2. The device of claim 1 wherein the liquid is a salt hydrate.

3. The device of claim 2 wherein the salt hydrate is selected from the group consisting of sodium acetate tetrahydrate, sodium acetate, sodium thiosulfate and trimethylol ethane hydrate.

4. The device of claim 1 wherein the receptacle is generally circular in shape and has an opening therethrough.

5. The device of claim 1 wherein the receptacle is generally cylindrical in shape and has a plug at each end thereof and wherein at least one of the plugs is in fluid communication with the container.

6. The device of claim 1 wherein the pressure is applied to the plurality of rigid objects by squeezing the trigger between a person's fingers.

7. The device of claim 1 wherein the container maybe conformable to a portion of a person's body.

8. A reusable device for delivering a release of heat to an area, the device comprising:
   (a) a liquid which releases heat upon crystallization;
   (b) a flexible, fluid-tight container to hold the liquid therein;

(c) a trigger to initiate the crystallization of the liquid, the trigger comprising a plurality of rigid objects comprised of ceramic or glass, and wherein the plurality of rigid objects are held within a receptacle located within the container, wherein the receptacle is in fluid communication with the container so that the plurality of rigid objects are in contact with the liquid, the trigger initiating the crystallization of the liquid when pressure is applied to the plurality of rigid objects.

9. A reusable device for delivering a release of heat to an area, the device comprising:

(a) a liquid which releases heat upon crystallization;

(b) a flexible, fluid-tight container to hold the liquid therein;

(c) a trigger to initiate the crystallization of the liquid, the trigger comprising a plurality of rigid objects being generally spherical in shape and having an approximate diameter of 1.5 mm, the rigid objects being comprised of a material selected from the group consisting of ceramic and glass, the plurality of rigid objects being held within a receptacle located within the container, wherein the receptacle is in fluid communication with the container so that the plurality of rigid objects are in contact with the liquid, the trigger initiating the crystallization of the liquid when pressure is applied to the plurality of rigid objects.

* * * * *